US00PP32144P2

(12) United States Plant Patent
Van Swieten

(10) Patent No.: US PP32,144 P2
(45) Date of Patent: Sep. 1, 2020

(54) ***PHALAENOPSIS* ORCHID PLANT NAMED 'PHALGAPVAL'**

(50) Latin Name: ***Phalaenopsis* hybrid**
Varietal Denomination: PHALGAPVAL

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/602,635

(22) Filed: Nov. 12, 2019

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ... A01H 5/02; A01H 5/00; A01H 5/08; A01H 6/62
See application file for complete search history.

*Primary Examiner* — June Hwu
(74) *Attorney, Agent, or Firm* — Jondle & Associates, P.C.

(57) ABSTRACT

A new and distinct variety of *Phalaenopsis* plant named 'PHALGAPVAL', particularly characterized by having light greenish-yellow flowers with white centers and yellow-white lips, peduncles that are medium long and moderately strong, leaves that are oblong, and is propagated by meristem tissue culture, is disclosed.

3 Drawing Sheets

Genus and species: *Phalaenopsis* hybrid.
Variety denomination: 'PHALGAPVAL'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGAPVAL'.

The new *Phalaenopsis* plant is a product of a planned breeding program conducted by the inventor in Bleiswijk, the Netherlands. The objective of this breeding program was to create a new *Phalaenopsis* plant with numerous attractive light greenish-yellow flowers with white centers and yellow-white lips, suitable for potted plant production.

The new *Phalaenopsis* plant 'PHALGAPVAL' is a result of cross-pollination made by the inventor in April 2009 in Bleiswijk, the Netherlands, of the proprietary female, or seed parent, *Phalaenopsis* hybrid '30317-01' (unpatented) with the proprietary male, or pollen parent, *Phalaenopsis* hybrid '01-1988' (unpatented).

The new *Phalaenopsis* was selected by the inventor as a single plant within the progeny of the stated cross-pollination in a controlled greenhouse in Bleiswijk, the Netherlands, in May 2012. Asexual reproduction of the new *Phalaenopsis* plant by meristem tissue culture since 2015 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Apr. 26, 2018, by Applicant who obtained the subject matter disclosed directly from the inventor. 'PHALGAPVAL' has not been made publicly available or sold anywhere in the world prior to the effective filing date of this application with the exception of sales or disclosures made one year or less before the effective filing date of this claimed invention by Applicant who obtained 'PHALGAPVAL' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALGAPVAL' as a new and distinct variety of *Phalaenopsis* plant:

1) Light greenish-yellow flowers with white centers and yellow-white lips;
2) Peduncle is medium long and moderately strong; and
3) Leaf shape is oblong.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in April 2019. Colors in the photographs may differ from the color values cited in the detailed botanical description, which accurately describe the actual colors of the new variety.

DESCRIPTION OF THE NEW VARIETY

Figure 1:
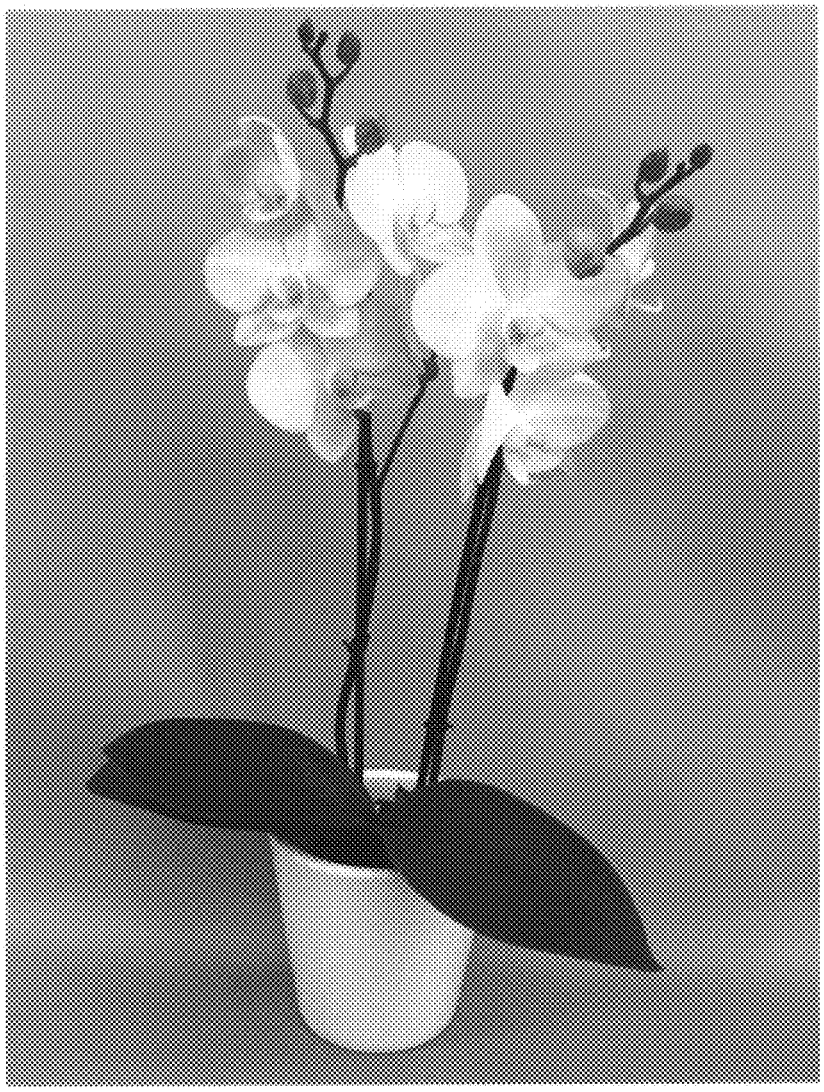
FIG. 1 shows the overall plant habit, including blooms, buds, and foliage of 'PHALGAPVAL'.
Figure 2:
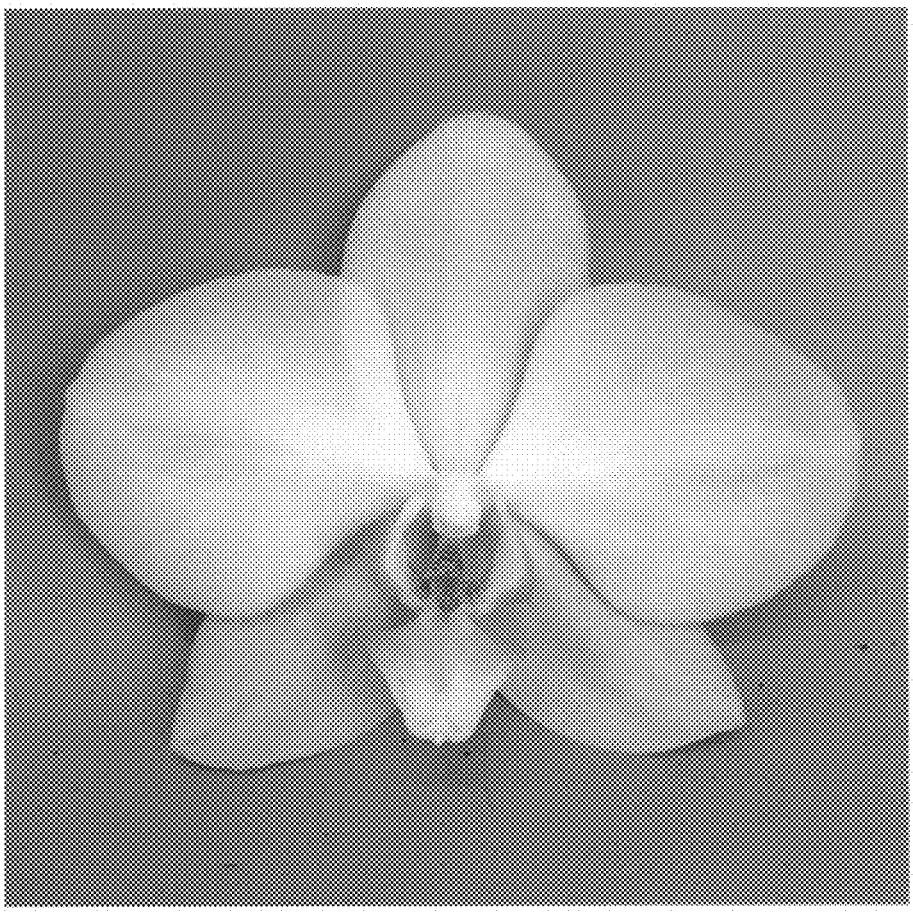
FIG. 2 shows a close-up of a flower of 'PHALGAPVAL'.
Figure 3:
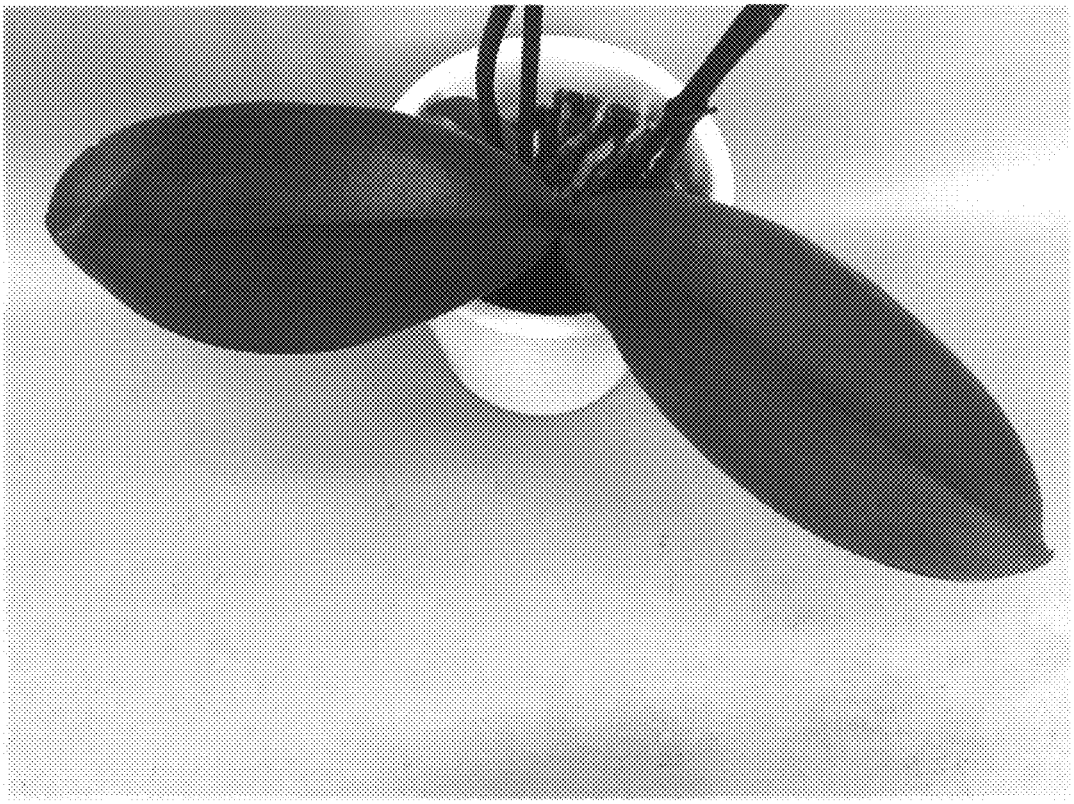
FIG. 3 shows an overhead view of the leaves of 'PHALGAPVAL'.

The following detailed description sets forth the distinctive characteristics of 'PHALGAPVAL'. Plants of the new

*Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in April 2019 on flowering plants which were planted in 12-centimeter (diameter) pots. After in-vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGAPVAL'.

Parentage:

*Female parent*.—*Phalaenopsis* cultivar '30317-01' (unpatented).

*Male parent*.—*Phalaenopsis* cultivar '01-1988' (unpatented).

Propagation:

*Type*.—Meristem tissue culture.

Roots:

*Root description*.—Greyed-green (between RHS 190B and 190C) colored roots with branching lateral roots having yellow-green (RHS 145A) colored root tips.

Plant:

*Commercial crop time to flowering*.—Following asexual propagation (in-vitro), the rooted cuttings grow for 20-24 weeks. After transplantation into 12-cm pots, the plants are finished after 48 to 50 weeks.

*Growth habit of peduncle*.—Upright to slightly pendant with raceme or panicle inflorescence.

*Height* (*from soil level to top of inflorescence*).—Approximately 43.0 cm to 48.0 cm.

*Width* (*measured from leaf tips*).—About 31.0 cm to 36.0 cm.

*Vigor*.—Moderate.

Leaves:

*Mature leaves*.—Quantity per plant: 6 to 8 leaves are produced before flowering. Length (fully expanded): 19.0 cm to 21.0 cm. Width: 7.0 cm to 8.0 cm. Shape: Oblong. Base shape: Moderately elongated. Apex: Acute and obtuse unequal. Leaf blade angle with the petiole (measured from the horizontal position): Between 15 degrees and 30 degrees. Leaf margin: Entire. Color: Upper surface: RHS 146A. Lower surface: RHS 146B and diluting dark red (RHS 187A). Texture (both upper and lower surfaces): Rough. Thickness: 2.0 mm to 3.0 mm. Variegation: Absent. Venation: Pattern: Parallel. Color of the midvein: Upper surface: RHS 146A. Lower surface: Diluting dark red (RHS 187A).

Peduncle:

*Quantity per plant*.—1 to 3.

*Number of flowers per peduncle*.—8 to 12.

*Length*.—43.0 cm to 48.0 cm.

*Diameter*.—5.0 mm to 6.0 mm.

*Strength*.—Moderately strong.

*Aspect*.—Upright to slightly pendant.

*Texture*.—Smooth.

*Color*.—Yellow-green (RHS 146C) with a touch of reddish-brown (RHS 200B).

*Internode length*.—4.0 cm to 5.0 cm.

Inflorescence description:

*Appearance*.—Upright to slightly pendant, raceme or panicle inflorescence with bilaterally symmetrical flowers that open in succession beginning with the lowermost flower.

*Number of inflorescences*.—1 to 2.

*Inflorescence size*.—Height (from base to tip): 200.0 mm to 250.0 mm.

*Flowering time*.—First flowers can be expected 10 to 11 months after planting in a 12-cm pot.

*Flower*.—Height: 83.0 mm to 88.0 mm. Diameter: 95.0 mm to 100.0 mm. Depth of lip: 22.0 mm to 24.0 mm.

*Flower longevity*.—On the plant: 15 to 19 weeks.

*Fragrance*.—Absent.

*Flower bud*.—Average size: Large. Length: 25.0 mm to 27.0 mm. Width: 20.0 mm to 22.0 mm. Shape: Egg shaped. Color: Light yellow-green (RHS 145B to 145C) with a touch of purplish-red (RHS N77D).

*Petals*.—Arrangement: Open/free. Shape: Semi-circular. Apex: Rounded asymmetric. Margin: Slightly undulated. Length (from base to tip): 43.0 mm to 45.0 mm. Width: 44.0 mm to 46.0 mm. Position of the broadest part of the petal: At the base. Color (when fully opened): Upper surface: Basic color: Light greenish-yellow (RHS, 1D). Over color: White (RHS NN155C) at the base. Lower surface: Basic color: Light greenish-yellow (RHS 1D). Over color: White (RHS NN155C) at the base.

*Dorsal sepal*.—Shape: Elliptic. Apex: Obtuse to rounded symmetric. Margin: Entire. Length (from base to tip): 48.0 mm to 50.0 mm. Width: 30.0 mm to 32.0 mm. Color (when fully opened): Upper surface: Basic color: Light greenish-yellow (RHS 1C). Over color: Slightly white (RHS NN155C) at the base. Lower surface: Basic color: Light greenish-yellow (RHS 1C). Over color: Slightly white (RHS NN155C) at the base and yellow-green (RHS 150C) in the middle.

*Lateral sepals*.—Shape: Ovate. Apex: Obtuse asymmetric. Margin: Entire. Length (from base to tip): 48.0 mm to 50.0 mm. Width: 28.0 mm to 30.0 mm. Color (when fully opened): Upper surface: Basic color: Light greenish-yellow (RHS 1C). Over color: White (RHS NN155C) at the base. Lower surface: Basic color: Yellow-green (RHS 150C). Over color: White (RHS NN155C) at the base and yellowish-green midvein (RHS N144A) toward the tip.

*Labellum* (*lip*).—Whiskers: Present. Length of whiskers: 6.0 mm to 8.0 mm. Color of whiskers: Light green-yellow (RHS 4C) at the base and RHS 5C toward the tip. Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Undulated. Length: 20.0 mm to 22.0 mm. Width: 11.0 mm to 13.0 mm. Color: White (RHS NN155C) with brownish-orange spots (RHS N170A) at the base and greenish-yellow (RHS 6A) on one side.

*Apical lobe*.—Shape: Trullate. Margin: Entire. Length: 20.0 mm to 22.0 mm. Width: 19.0 mm to 21.0 mm. Color: Greenish-yellow (RHS 2A to 2B) at the base and midvein; white (RHS NN155C) toward whiskers.

*Callus*.—Average size: Medium. Height: 5.0 mm to 6.0 mm. Length: 4.0 mm to 5.0 mm. Width: 4.0 mm to 5.0 mm. Color: Yellow (RHS 8A); dotted (RHS N172A).

Reproductive organs:

*Column*.—Length: 8.0 mm to 10.0 mm. Diameter: 5.0 mm to 6.0 mm. Color: White (RHS NN155C).

*Pollinia*.—Quantity: 2. Diameter: 0.8 mm to 1 0 mm. Color: Orange (RHS 23A).

*Ovary*.—Length: 11.0 mm to 13.0 mm. Diameter: 2.2 mm to 2.4 mm. Color: Light yellow-green (RHS 145C to 145D) with a touch of very light purple (RHS 76C) toward the flower.

*Pedicel*.—Length: 30.0 mm to 32.0 mm. Diameter: 2.6 mm to 2.8 mm. Color: Light yellow-green (RHS 145B) at the base and lighter yellow-green (RHS 145C) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGAPVAL' differs from female parent plant '30317-01' (unpatented) in that 'PHALGAPVAL' has flowers with a basic color of light greenish-yellow, whereas '30317-01' has flowers with a basic color of yellow. Additionally, 'PHALGAPVAL' has larger-flowers than '30317-01'.

'PHALGAPVAL' differs from male parent plant '01-1988' (unpatented) in that 'PHALGAPVAL' has flowers with a basic color of light greenish-yellow, whereas '01-1988' has flowers with a basic color of white. Additionally, 'PHALGAPVAL' has smaller flowers than '01-1988'.

'PHALGAPVAL' is most similar to the commercial *Phalaenopsis* plants named 'PHALFIMWAQ' (U.S. Plant Pat. No. 26,067) and 'PHALGLAZAL' (U.S. Plant Pat. No. 29,909). 'PHALGAPVAL' differs from the commercial variety 'PHALFIMWAQ' in that 'PHALGAPVAL' has obtuse to rounded dorsal sepal apexes and calluses with a basic color of yellow, whereas 'PHALFIMWAQ' has emarginated dorsal sepal apexes and calluses with a basic color of orange.

'PHALGAPVAL' differs from the commercial variety 'PHALGLAZAL' in that 'PHALGAPVAL' has obtuse to rounded dorsal sepal apexes and trullate apical lobes, whereas 'PHALGLAZAL' has emarginated dorsal sepal apexes and rhombic apical lobes. Additionally, 'PHALGAPVAL' has larger flowers than 'PHALGLAZAL'.

I claim:

1. A new and distinct variety of *Phalaenopsis* plant named 'PHALGAPVAL', substantially as described and illustrated herein.

* * * * *